United States Patent
Farag et al.

(10) Patent No.: US 10,242,444 B1
(45) Date of Patent: Mar. 26, 2019

(54) SEGMENTATION OF THE COLON FOR ACCURATE VIRTUAL NAVIGATION

(71) Applicants: Amal Farag, Louisville, KY (US);
Salwa Elshazly, Louisville, KY (US)

(72) Inventors: Amal Farag, Louisville, KY (US);
Salwa Elshazly, Louisville, KY (US)

(73) Assignee: Kentucky Imaging Technologies, LLC, Louisville, KY (US)

( * ) Notice: Subject to any disclaimer, the term of this patent is extended or adjusted under 35 U.S.C. 154(b) by 0 days.

(21) Appl. No.: 15/392,432

(22) Filed: Dec. 28, 2016

Related U.S. Application Data

(60) Provisional application No. 62/272,649, filed on Dec. 29, 2015.

(51) Int. Cl.
*A61B 6/03* (2006.01)
*G06T 7/00* (2017.01)
*G06T 7/11* (2017.01)

(52) U.S. Cl.
CPC ............ *G06T 7/0012* (2013.01); *A61B 6/032* (2013.01); *G06T 7/11* (2017.01); *G06T 2207/10081* (2013.01); *G06T 2207/30061* (2013.01)

(58) Field of Classification Search
CPC combination set(s) only.
See application file for complete search history.

(56) References Cited

U.S. PATENT DOCUMENTS

| | | | | |
|---|---|---|---|---|
| 2003/0223627 A1* | 12/2003 | Yoshida | ............... | G06T 7/0012 382/128 |
| 2009/0012382 A1* | 1/2009 | Dutta | ................. | A61B 5/02007 600/407 |
| 2010/0189326 A1* | 7/2010 | McGinnis | ............. | G06T 7/0012 382/131 |
| 2011/0206250 A1* | 8/2011 | McGinnis | ............. | G06T 7/0012 382/128 |
| 2013/0170723 A1* | 7/2013 | Kwon | ..................... | G06T 7/155 382/131 |

\* cited by examiner

*Primary Examiner* — Tsung Yin Tsai
(74) *Attorney, Agent, or Firm* — Law Office of J.L. Simunic; Joan L. Simunic

(57) ABSTRACT

The present development is a method for generating a computer-aided accurate segmentation of an irregular structure, such as a colon The approach is based on a multi-tiered information propagation framework using statistical and variational methods. First, an initial segmentation using a method such as intensity based or shape-model registration for a volume of a typical CT is generated. The segmented image is subjected to a global/convex continuous minimization approach. After minimization, the data goes through post processing, and then the final segmented irregular structure output volume is generated.

13 Claims, 3 Drawing Sheets

SEGMENTATION OF THE COLON FOR ACCURATE VIRTUAL NAVIGATION

CROSS-REFERENCE TO PRIOR APPLICATIONS

The present application claims priority to U.S. Patent Application 62/272,649 filed 2015 Dec. 29, which is incorporated by reference in its entirety.

FIELD OF THE INVENTION

The present invention is a method for segmenting an object for three-dimensional visualization of an internal organ using a any computer-aided diagnosis system.

BACKGROUND OF THE INVENTION

In a virtual colonography (VC) the patient undergoes a CT (computed tomography) scan, and the data are used to create a 3D or 2D representation of the colon. VC aims to quantify the internal texture of the colon. Common VC visualization techniques include the virtual Fly-Through (FT) and virtual Fly-Over (FO). Both simulate a real colonoscopy by moving a virtual camera with a specific field of view along a planned path inside the colon, rendering internal views.

An essential aspect of any computer-aided diagnosis colonography system is a means to have accurate segmentation of the colon. Colon segmentation is a challenging problem because the colon is highly topologically variable, it is an asymmetrically askew organ (i.e. Haustral folds), and Hounsfield intensity regions consistent with air, soft tissue and high-attenuation structures define the various regions of the colon. The presence of residual stool, lesions, and disconnected colon segments further add to the difficulties of virtual visualization.

In the academic literature both semi-automated and fully-automated colon segmentation algorithms have been proposed. In general, automated approaches use a combination of region growing and tissue classification. The prior art teaches region growing based on gradient magnitude and distance transforms and deformable geometric models. These techniques can be inaccurate, complex and expensive. Tissue classification methods include simple thresholding and principle component analysis.

Knowledge-based or anatomy-based colon segmentation algorithms have also been used. One two-step method utilizes region growing to extract extra segmented regions, such as the small bowel and stomach, in conjunction with an "anatomy-based extraction" that removes outer-air, bone and lung regions to enhance initial segmentation results. Lu et al. proposed a two-tiered approach that consists of a pre-segmentation step that classifies regions in the abdominal cavity as colon or extra-colonic (i.e. stomach, small bowel, etc.) using statistical modeling on geometry based features. The output is evaluated using a colon tracking algorithm, "daisy-chaining", integrated with distance and geometry statistics per patient to handle moderately or poorly distended colon regions. However, these methods are not highly effective for segmenting the colon.

Thus, a method is needed that will provide more accurate segmentation of the colon or other irregular shaped structure. The present development aid in virtual colonography by creating a more defined and complete representation of the organ. The approach requires minimal memory and computational time while preserving VCs benefits for clinicians and patients.

SUMMARY OF THE PRESENT INVENTION

The present development is a method for generating a computer-aided accurate segmentation of an irregular structure, such as a colon. The approach is based on a multi-tiered information propagation framework using statistical and variational methods. First, an initial segmentation of a typical CT is generated. The initial segmented volume is sent through a 3D global convexification minimization formulation of variational methods to extract contrast filled and high attenuation areas that are part of the irregular structure. The 3D volume then undergoes post processing to receive the final 3D representation of the irregular structure, such as the colon.

DETAILED DESCRIPTION OF THE PRESENT DEVELOPMENT

The present development is a method for generating a computer-aided accurate segmentation of an irregular structure, such as a colon. The approach is based on a multi-tiered information propagation framework using statistical and variational methods. The steps comprise: (a) generating an initial segmentation; (b) generalizing a global/convex formulation of the variational method into a 3D space to obtain the remaining contrast-filled or high-attenuation areas or both considered part of the irregularly shaped structure that was not extracted in step (a); and, (c) post processing to provide a final segmentation of the connected colon.

The initial segmentation of a typical CT produces a rough segmentation of the desired irregular shape and may be generated by methods known in the art. In a preferred embodiment, the initial segmentation is achieved by using an intensity histogram based method that utilizes expectation maximization to obtain a threshold that encompasses air and soft tissue regions from a CT scan. In an alternative embodiment, the initial segmentation is achieved by using a shape-based method. Post processing may be achieved by various methods known in the art, such as but not limited to 3D connected component with morphological operations or region growing.

Figure 1:
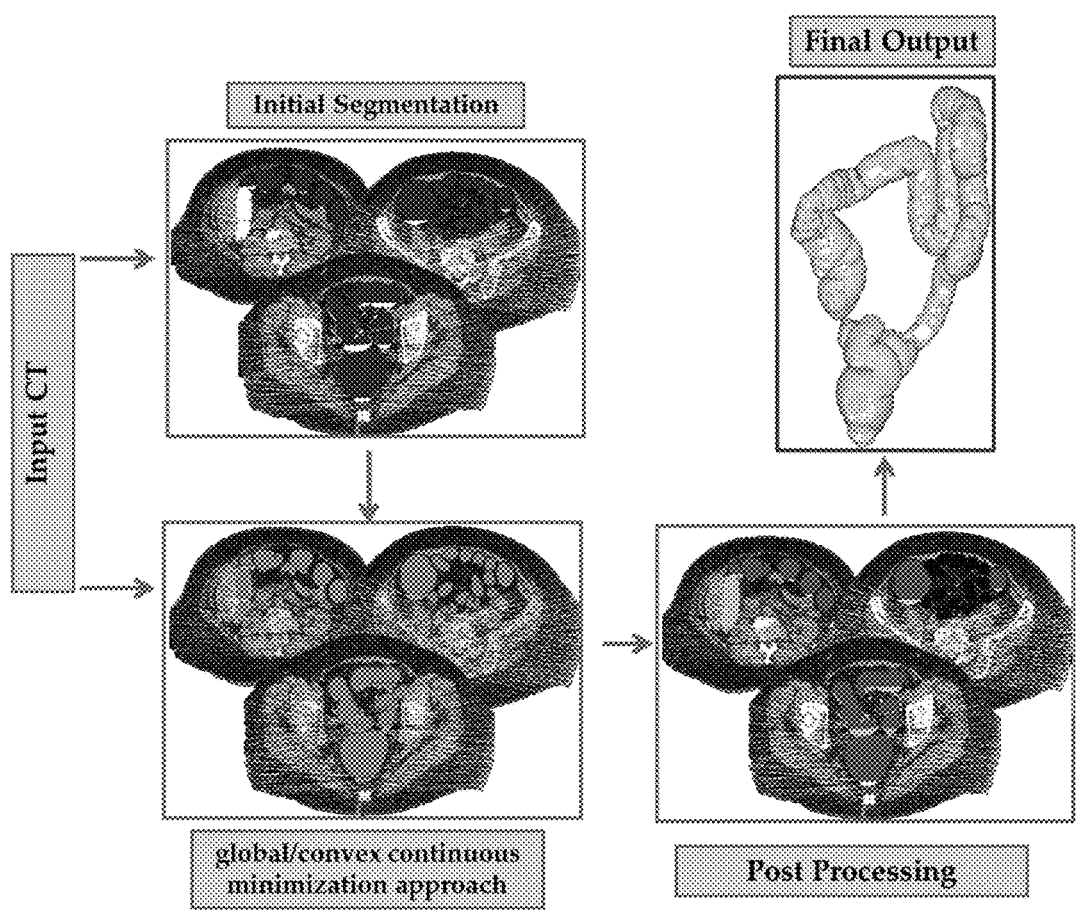
FIG. 1 is a schematic of the overall segmentation approach from CT data volume to final 3D model representation.

A pictorial graphic of the images generated from each step of the present process is shown in FIG. 1. An initial segmentation using the intensity histogram volume of a typical computed tomography (CT) is generated. Expectation maximization is then used to obtain a threshold intensity that encompasses the colon air regions and soft tissue. The Mumford-Shah global/convex continuous minimization problem of the active contour model (GAC) and the Chan-Vese active contour model without edges model (ACWE) are generalized to the 3D-space and are mathematically manipulated enhancing the reconstruction of the topological changes of Haustral folds while maintaining polyps on the colon walls. Post processing in the form of 3D connected component and morphological operations can provide the final segmentation of connected colons. Overall voxel surface and organ information is used to enhance post processing of retaining disconnected organ information.

The variational model is defined by the two-phase piecewise constant approximation of the Mumford-Shah model:

$$\min_{\Omega_l c_1 c_2} \left\{ E_{ACWE}(\Omega_l, c_1 c_2, \lambda) = \text{per}(\Omega_l) + \lambda \int_{\Omega_l} (c_1 - (I(x))^2 dx + \lambda \int_{\Omega/\Omega_l} (c_2 - (I(x))^2 dx \right\} \quad \text{Eq. 1}$$

where I is the given image, $\lambda$ is a positive parameter controlling the tradeoff between regularization process and fidelity of solution with respect to I, $\Omega_I$ is a closed subset of the image domain $\Omega$, per $(\Omega_I)$ is its perimeter, and $c_1 c_2 \in R$. To allow the solution of Eq. 1 to be a non-convex formula the energy function based on the gradient descent flow is adapted allowing the energy function to obtain the global minimum solution for any parameter >0: (u, $c_1 c_2$, $\lambda$)=$TV_g$ (u)+$\lambda \int r_1(x, c_1, c_2)$u dx, based on the weighted total variation (TV) of a function u with a weight function g, that contains information concerning the boundaries of an image $I_o$ given by:

$$g(|\nabla I_o|) = \left( \frac{1}{1 + \beta |\nabla I_o|^2} \right),$$

and $\beta$ is an arbitrary positive constant. This provides the link between the active contour without edge (ACWE) and global/convex continuous minimization of the active contour model (GAC) when g is an edge indicator function and u is a characteristic function. Extending the proposed numerical solution to 3D, the discrete gradient operator can be given by:

$$(\nabla u)_{i_x, i_y, i_z} = ((\nabla u)^1_{i_x, i_y, i_z}, (\nabla u)^2_{i_x, i_y, i_z}, (\nabla u)^3_{i_x, i_y, i_z}) \quad \text{Eq. 2}$$

Figure 2:
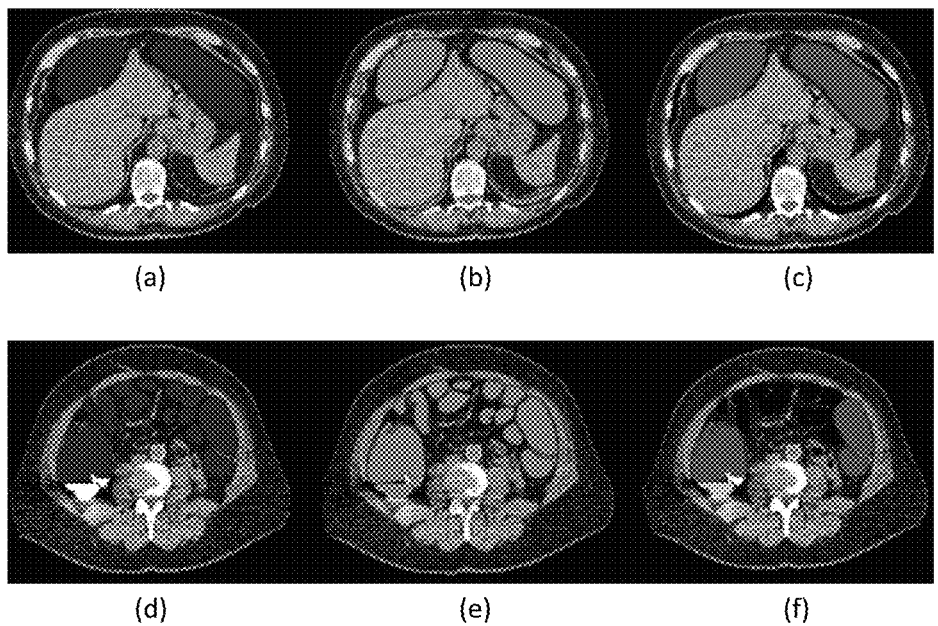
FIG. 2 shows two-dimensional results for a patient showing the results after various stages of data processing: (a) is the initial segmentation; (b) after GAC implementation; and (c) final results after post-processing.

FIG. 2 shows exemplary two-dimensional slice results of the segmentation process for the same patient from two different segments of the colon. The initial statistical approach based segmentation, shown in images 2(a) and 2(f), provides results of anatomical structures such as low intensity colon regions, small bowel and lungs. The global convexification approach is used to identify high intensity contrast filled regions that are part of the colon and enhance segmentation around the colon lumen and haustral folds, as shown in images 2(b) and 2(e). As shown in images 2(c) and 2(f), connected component analysis in conjunction with 3D connected component analysis keeping only the largest overall connected component provides the final segmentation result.

Figure 3:
FIG. 3 shows two-dimensional slice and 3D volume results of a disconnected colon using shape modeling, global convexification approach, and region growing; and, FIG. 4 shows 3D segmentation results from two different patients in comparison to the groundtruth manual segmentation.

FIG. 3 shows an exemplary two-dimensional slice and 3D volume results of a disconnected colon using shape modeling for the initial segmentation, global convexification approach to identify high intensity contrast filled regions, and region growing. Such a case is very challenging and the framework shows robustness and accuracy in obtaining the colon surface.

Figure 4:
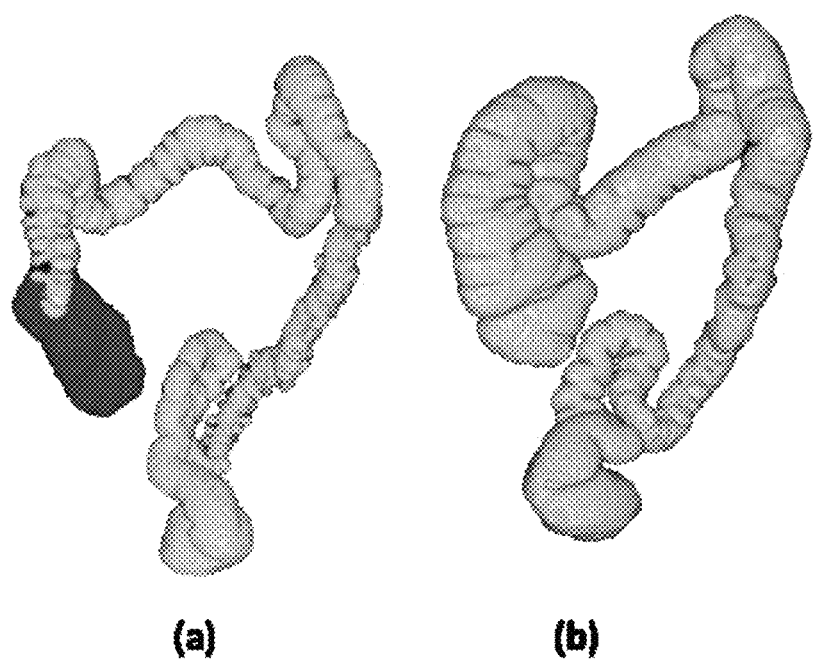

FIGS. 4(a) and 4(b) are 3D reconstructions of colons from two different patients after post-processing. The images in FIGS. 4(a) and 4(b) are compared to groundtruth manual segmentation. More specifically, FIG. 4(a) shows a colon reconstruction where the transverse and ascending colon had considerable amounts of air, residual stool and contrast creating difficulties in accurately segmenting the cecum. The result was a 78.0% Sorensen index (Dice) coefficient and caused the area shown in the far left (highlighted in red) to be considered a secondary component not connected to the colon. FIG. 4(b) did not have the same contrasting difficulties of FIG. 4(a) and had a 93.8% Dice coefficient, resulting in a much more accurate segmentation and final output. FIG. 4(a) segmentation is enhanced when the overall voxel surface information of typical colons is utilized in conjunction with the connected component analysis and morphological dilation operations. A subset from the ACRIN study (30 supine oral contrast enhanced abdominal CT scans) is used to assess the accuracy and robustness measures for colon segmentation. In both FIG. 4(a) and FIG. 4(b), the areas in red represent the highest variation from groundtruth volume.

As compared to the prior art, the method of the present development shows promise in its ability to obtain both air-filled and fluid-filled (contrast enhanced) colon regions for datasets of size 512×512×N dataset, where N refers to the number of slices within a volume. An especially promising feature of the present development is its ability to obtain both air-filled and fluid-filled (contrast enhanced) colon regions in 2 to 3 minutes for datasets of size 512×512×400, with just a slight increase in time as the dataset size increases to over 600 slices.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. Thus, for example, reference to "a scan" includes a plurality of such scans, and so forth.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

It is understood that, in light of a reading of the foregoing description, those with ordinary skill in the art will be able to make changes and modifications to the present invention without departing from the spirit or scope of the invention, as defined herein.

What is claimed is:

1. A method for generating an enhanced computerized image of an irregularly-shaped structure, the method comprising:
   a. generating an initial segmentation of the irregularly-shaped structure that encompasses air regions and soft tissue;
   b. after obtaining the initial segmentation output, generalizing a global/convex formulation to obtain the contrast-filled areas or high-attenuation areas or a combination thereof that were not extracted in step (a), wherein the global/convex formulation is a generalization of a variational method into a 3D space, and wherein the variational model is defined by the two-phase piecewise constant approximation of the Mumford-Shah model:

$$\min_{\Omega_I c_1 c_2} \left\{ E_{ACWE}(\Omega_I, c_1 c_2, \lambda) = \text{per}(\Omega_I) + \lambda \int_{\Omega_I} (c_1 - (I(x))^2 dx + \lambda \int_{\Omega/\Omega_I} (c_2 - (I(x))^2 dx \right\}$$

where I is the given image, $\lambda$ is a positive parameter controlling the tradeoff between regularization process and fidelity of solution with respect to I, $\Omega_I$ is a closed subset of the image domain $\Omega$, per $(\Omega_I)$ is its perimeter, and $c_1 c_2 \in R$, and,
   c. post processing to provide a final segmentation of the irregularly-shaped structure.

2. The method of claim 1 wherein the initial segmentation produces a rough segmentation of the desired irregular shape.

3. The method of claim 2 wherein the initial segmentation of the irregularly-shaped structure is achieved by using an intensity histogram based method or a shape-model based method.

4. The method of claim 3 wherein the intensity histogram based method is an intensity histogram based method utilizing expectation maximization which is used to obtain a threshold that encompasses lower threshold intensity areas, air and soft tissue regions from a colonography CT scan, and combinations thereof.

5. The method of claim 1 wherein the global/convex formulation comprises the Mumford-Shah global/convex continuous minimization problem of the active contour model (GAC) and the Chan-Vese active contour model without edges model (ACWE).

6. The method of claim 1 wherein the energy function based on the gradient descent flow is adapted allowing the energy function to obtain the global minimum solution for any parameter >0: $E_1(u, c_1 c_2, \lambda) = TV_g(u) + \lambda \int r_1(x, c_1, c_2) u \, dx$, based on the weighted total variation (TV) of a function u with a weight function g, that contains information concerning the boundaries of an image $I_o$ given by:

$$g(|\nabla I_o|) = \left( \frac{1}{1 + \beta |\nabla I_o|^2} \right),$$

and $\beta$ is an arbitrary positive constant.

7. The method of claim 6 wherein g is further an edge indicator function and u is further a characteristic function, and wherein the proposed numerical solution is expanded to three dimensions by defining the discrete gradient operator according to the equation:

$$(\nabla u)_{i_x, i_y, i_z} = ((\nabla u)^1_{i_x, i_y, i_z}, (\nabla u)^2_{i_x, i_y, i_z}, (\nabla u)^3_{i_x, i_y, i_z}).$$

8. The method of claim 1 wherein the post processing comprises 3D connected component operations or morphological operations or a combination thereof.

9. The method of claim 1 wherein the post processing comprises a connected component analysis with morphological operations method or a region growing method.

10. The method of claim 1 wherein the irregularly-shaped structure is a colon.

11. The method of claim 7 wherein the initial segmentation step (b) produces a digitized image readable by a computer program of low intensity colon regions, the small bowel, the lungs and combinations thereof.

12. The method of claim 7 wherein the global/convex formulation generalization step (c) produces a digitized image readable by a computer program of high intensity contrast filled regions that are part of the colon, colon lumen, haustral folds and combinations thereof.

13. The method of claim 1 wherein the enhanced computerized image of the irregularly-shaped structure can be obtained using a 512×512×N dataset, wherein N refers to the number of slices within a volume.

* * * * *